United States Patent [19]

Mohan et al.

[11] 4,146,470
[45] Mar. 27, 1979

[54] USE OF MICROORGANISMS IN COMBINATION WITH SURFACE ACTIVE AGENTS TO SYNERGISTICALLY DISPERSE OIL SLICKS

[75] Inventors: Raam R. Mohan, Berkeley Heights; Max L. Robbins, South Orange, both of N.J.; Allen I. Laskin, New York, N.Y.; Lars A. Naslund, Morganville, N.J.

[73] Assignee: Exxon Research & Engineering Co., Florham Park, N.J.

[21] Appl. No.: 818,191

[22] Filed: Jul. 22, 1977

Related U.S. Application Data

[63] Continuation of Ser. No. 457,098, Apr. 1, 1974, abandoned.

[51] Int. Cl.² .............................................. C12B 1/100
[52] U.S. Cl. ........................................... 210/2; 210/11; 210/59; 210/DIG. 27; 195/3 H; 252/312

[58] Field of Search ......... 210/2, 11, 40, 59, DIG. 27; 195/3 H; 252/312, 354, 356

[56] References Cited

U.S. PATENT DOCUMENTS

| | | | |
|---|---|---|---|
| 2,447,551 | 8/1948 | Zisman et al. | 252/312 |
| 3,293,145 | 12/1966 | Leavitt et al. | 195/3 H |
| 3,769,164 | 10/1973 | Azarowicz | 210/11 |
| 3,793,218 | 2/1974 | Canevari | 252/312 |
| 3,843,517 | 10/1974 | McKinney et al. | 210/11 |
| 3,871,957 | 3/1975 | Mohan et al. | 210/11 |
| 3,959,134 | 5/1975 | Canevari | 210/DIG. 27 |

*Primary Examiner*—Charles N. Hart
*Assistant Examiner*—Benoit Castel
*Attorney, Agent, or Firm*—John P. Corcoran; Joseph J. Allocca

[57] ABSTRACT

A method of preparation and application of a composition comprising specified microorganisms in combination with surfactants for a synergistic dispersal of oil slicks.

3 Claims, No Drawings

USE OF MICROORGANISMS IN COMBINATION WITH SURFACE ACTIVE AGENTS TO SYNERGISTICALLY DISPERSE OIL SLICKS

This is a continuation, of application Ser. No. 457,098, filed Apr. 1, 1974.

This invention relates to the utilization of microorganisms in combination with chemical surfactants for rapid and effective dispersing of oil slicks.

Pollution of rivers, streams, harbors, bays, beaches and the open ocean by crude oil and various refined products has been an increasingly important problem. On ocean waters a highly visible film having an area of about one square mile can be formed with only 50 gallons of oil. Such oil slicks or films are undesirable not only from an aesthetic standpoint, but also because cohesive oil films represent a barrier to the transfer of oxygen from the atmosphere to marine life and a serious hazard to marine fowl.

The pollution of water by oil is sometimes inadvertently occasioned by the discharge of ballast water from oil tankers or from offshore drilling operations, and by disasterous accidental collisions, groundings or breakups of tankers. The latter have become more of a threat in recent years because of the tremendous increase in the quantity of crude oil and refined products being transported by water. While the discharge of oil to the water in these situations is sought to be avoided, accidents nevertheless do occur.

Various techniques have been advanced for solving the oil contamination problem. One solution involves the use of strong detergents to emulsify the oil with the water. Other dispersants for emulsifying the oil with the water have also been suggested. However, the use of strong detergents has resulted in severe damage to marine life. Other dispersants, while nontoxic, have not always proven effective for dispersing highly viscous sea-borne oil slicks.

In accordance with the present invention, it has been found that there is a synergistic effect, resulting in rapid and efficient dispersion of intact cohesive oil films or slicks, when specified microorganisms are used in combination with various chemical surfactants. The use of the synergistic mixtures allows for a marked reduction in the quantity of chemical surfactant or detergent necessary, for dispersion, resulting in benefits in terms of both more favorable economics and less potential upset to the environment and the ecology.

Although it is believed that most microorganisms would be useful in this application, those that have actually been utilized are tabulated hereinbelow along with their corresponding American Type Culture Collection (A.T.C.C.) Registration Numbers which are secured by depositing these cultures with the American Type Culture Collection 212 M. Street, N.W., Washington, D.C.

| Microorganism | ATCC # |
| --- | --- |
| *Micrococcus cerificans* | 14987 |
| *Corynebacterium* sp. | 21235 |
| *Candida utilis* | 9226 |
| *Arthrobacter* sp. | 21908 |
| *Micrococcus* sp. | 21909 |
| *Achromobacter* sp. | 21910 |

The chemical dispersants which are useful in mixing with these microorganisms are broadly sorbitan monooleates, polyoxyalkylene adducts of the sorbitan monoesters and dialkyl sulfosuccinate salts. These dispersants can be either water based or hydrocarbon based and they exhibit hydropilic-lipophilic balance numbers ranging from 5.0 to 14.

Specific dispersants employed were as follows: sorbitanmonoleate (available as SPAN 80 from Atlas Chemical Company) and polyoxyethylene adduct of sorbitanmonoleate (available as TWEEN 80 from Atlas Chemical Company).

Anionic surfactants comprising water-dispersible salts of dialkyl sulfosuccinates wherein the alkyl group is a branched chain radical containing 8 or 9 carbon atoms were also employed.

The preferred anionic surfactant, useful in this invention, is sodium dioctylsulfosuccinate or more precisely, sodium di(2,ethylhexyl)sulfosuccinate. This surfactant is commercially available under various trade names such as "Aerosol OT" made by American Cyanamid Company of Wayne, New Jersey.

These dispersants may be either undiluted or diluted with a liquid organic medium in which the dispersant composition is either soluble or dispersible. Examples of suitable liquid media include the isoparaffinic and cycloparaffinic (naphthenes) hydrocarbons boiling within the range between about 210° F. and 500° F. such as 2,2,5-trimethylhexane; 2,6-di-methylheptane; 4-ethylheptane; cycloheptane and the like. For economic reasons, it would be preferable to use commercial petroleum solvents which are mixtures of various isoparaffins and cycloparaffins. Said solvents are available from the EXXON Refining Company under the trade names of "Isopar E", "Isopar G", "Isopar H", "Isopar K" "Isopar L" and "Isopar M". The dispersant composition of this invention can be mixed in a liquid organic medium in any desired portion. Generally, it is desirable to mix one part by volume of dispersant composition herein (solvent-free base) with up to about 3 parts by volume of the liquid organic medium.

The concentration of the various microorganisms, as well as the dispersants are based upon the use of 100 parts by weight of oil. The ratio of microorganism ranges from one half to 10 parts by weight of microorganism per one hundred parts by weight of oil. The preferred range of microorganisms is from 5 parts to 2 parts by weight per one hundred parts by weight of oil. The chemical dispersant as described hereinabove per 100 parts by weight of oil ranges from 0.5 to 20 parts by weight and preferably from 1 to 5 parts by weight.

The various oils used in this experiment are No. 4 heating oil, Southern Louisiana crude, Prudhoe Bay crude, LaRosa crude and Kuwait crude oils. It is believed that the source of the crude does not have any bearing on the synergistic effect of mixing the dispersant solution with the microorganisms in the manner taught in the subject application.

The dispersant composition of the invention has a hydrophilic-lipophilic balance (HLB) ranging from 5.0 to 14.0. The HLB value of dispersant composition is an important property since it has been found that this value determines whether the composition will be an effective oil slick dispersant under conditions of use. For the purposes of the instant invention, the hydrophilic-lipophilic balance number (HLB) is determined according to the following equation:

$$HLB = \Sigma \frac{\frac{\text{(Mol. Wt. of Hydrophilic compound used in synthesis of Component A)}}{\text{(Mol. Wt. Component A)}} (20) \text{(Wt. \% of A in Dispersant)}}{} +$$

$$\frac{\frac{\text{(Mol. Wt. of hydrophilic compound used in synthesis of Component B)}}{\text{(Mol. Wt. Component B)}} (20) \text{(Wt. \% of B}^+ \text{ in Dispersant)}}{}$$

In summary, HLB number is ascertained by dividing the molecular weight of the hydrophilic compounds employed in the synthesis of a given compound by the molecular weight of that compound and multiplying the result by 20. In situations where a plurality of materials are employed in the dispersant system, the HLB number for the total system is the summation of the HLB numbers of the individual components multiplied by the weight percent of that particular component of the total dispersant system.

The invention will be further illustrated by reference to the following examples.

EXAMPLE 1

For the purposes of tests, the following dispersant mixtures were made by mixing the components together in a manner set forth in the following Table on a weight percent basis.

TABLE I

| Dispersants | | Wt.% Dispersant Composition | | |
|---|---|---|---|---|
| Component | Component HLB | 1* (1) | 2* (2) | 3* (3) |
| "Span 80" (sorbitan monooleate) | 4.3 | 9 | 21 | 9 |
| "Tween 80" (sorbitan monooleate ethylene oxide adduct - 20 moles | 15.0 | 91 | 7 | 15 |
| "Aerosol OT" (aqueous sodium dioctyl sulfosuccinate, 75%) | 10.0 | — | — | 15 |
| "Isopar M" (isoparaffinic hydrocarbon solvent) | | — | 72 | 61 |
| HLB | | 14.0 | 7.0 | 10.6 |

1* Mixture 1
2* Mixture 2
3* Mixture 3

EXAMPLE 2

A series of tests were conducted to demonstrate the increased effectiveness of employing dispersants in combination with microorganisms for dispersing oil in sea water. The general test procedure consisted of adding 800 mg oil (100 parts by weight) to a standard 500 ml Erlenmeyer flask containing 200 ml of sea water (Rila Marine Mix or actual sea water). The microorganisms, or the chemical dispersant, or a mixture of dispersant and microorganisms (parts by weight based on amount of oil) is added to the flask. The flask is then placed on a Gyrotory shaker at 100 rpm and 25° C. and sampled at various times. The sample is extracted with chloroform and the percent transmission is compared with the standard curve prepared for the oil of choice and the percent of oil dispersed is calculated. The results of this series of tests are shown in Table II.

TABLE II

| Ratio (By Wt) Kuwait Crude Oil : Dispersant | Mixture | % Dispersion After Various Times (Min.) | | | | | | |
|---|---|---|---|---|---|---|---|---|
| | | 5 | 15 | 30 | 45 | 60 | 90 | 120 |
| 100 : 1 | 3 | 19 | 20 | 27 | 35 | 48 | 53 | 36 |
| 100 : 5 | 3 | 55 | 72 | 90 | 90 | 90 | 90 | 90 |
| 100 : 10 | 3 | 66 | 77 | 94 | 94 | 94 | 100 | 100 |
| 100 : 1 | 2 | 56 | 60 | 66 | 63 | 45 | 42 | 40 |
| 100 : 10 | 2 | 78 | 82 | 84 | 85 | 86 | 95 | 95 |
| 100 : 1 | 1 | 40 | 44 | 50 | 30 | 30 | 20 | 20 |
| 100 : 10 | 1 | 52 | 50 | 62 | 73 | 83 | 73 | 52 |
| 100 : 20 | 1 | 32 | 33 | 60 | 78 | 85 | 80 | 78 |

In this example, the dispersant preparations designated Mixture 3, Mixture 2 and Mixture 1 were tested for their ability to disperse a sample of Kuwait crude oil, using the ratios of oil:dispersant indicated in Table II. It will be noted that for effective and lasting dispersion of the oil under these conditions, the oil:dispersant ratio must be approximately 100:5 for Mixture 3, 100:10 for Mixture 2 and 100:20 for Mixture 1. Several of these experiments were repeated, this time using only 1 part of each dispersant per 100 parts of oil, but in some flasks, 1 part (by dry weight) of a preparation of the microorganism *Micrococcus cerificans* ATCC 14,987 was added either alone, or in addition to the chemical dispersant. The results of this series of tests are shown in Table III.

TABLE III

| Ratio (By Wt.) Kuwait Oil:Dispersant: Microorganism | | | % Dispersion After Various Times (Min.) | | | | | | |
|---|---|---|---|---|---|---|---|---|---|
| | Mixture | ATCC 14,987 | 5 | 15 | 30 | 45 | 60 | 90 | 120 |
| 100 : 1 | 3 | 0 | 10 | 11 | 1 | 1 | 5 | 10 | 15 |
| 100 : 0 | | 1 | 22 | 17 | 14 | 14 | 25 | 30 | 30 |
| 100 : 1 | 3 | 1 | 15 | 35 | 38 | 48 | 59 | 56 | 56 |
| 100 : 1 | 2 | 0 | 56 | 60 | 66 | 63 | 45 | 42 | 40 |
| 100 : 0 | | 1 | 25 | 30 | 35 | 36 | 36 | 34 | 28 |
| 100 : 1 | 2 | 1 | 56 | 75 | 80 | 82 | 85 | 79 | 75 |
| 100 : 1 | 1 | 0 | 35 | 45 | 60 | 52 | 45 | 35 | 15 |
| 100 : 0 | | 1 | 1 | 1 | 25 | 25 | 27 | 30 | 30 |
| 100 : 1 | 1 | 1 | 35 | 45 | 62 | 65 | 68 | 73 | 70 |

In these experiments, the dispersions caused by the low level of chemical dispersant used alone was in each instance incomplete and impermanent; the dispersed oil began to coalesce into a coherent film after 1 or 2 hours. The microorganism used alone, at the ratio of 100 parts of oil to 1 part of microorganism, resulted in in a modest degree of dispersion, usually about 30%, which was stable for the period of experimentation. In each case where both materials were used, there was a dramatic improvement in both the degree and stability of the dispersion.

EXAMPLE 3

The procedure of Example 1 was followed except that two other microorganisms, the bacterium Corynebacterium sp. (ATCC 21,235), and the yeast *Candida utilis* (ATCC 9226) were substituted. These tests were done using the chemical dispersant Mixture 2. The results are shown in Table IV. Neither of these microorganisms, when used alone at the ratio of 100 parts of oil to one part of microorganism, were at all effective in dispersing the oil. The low level of dispersant (100:1 ratio) was, again, only moderately effective, but in each instance where both agents (microorganism plus chemical dispersant) were used, a very striking improvement in effectiveness (rapidity and persistence) of dispersion of the oil was noted.

TABLE IV

| Ratio (By Wt.) Kuwait Oil:Dispersant:Microorganism | | | % Dispersion After Various Times (Min.) | | | | | | |
|---|---|---|---|---|---|---|---|---|---|
| | Mixture 2 | (ATCC #) | 5 | 15 | 30 | 45 | 60 | 90 | 120 |
| 100 : | 1 : | 0 | 15 | 22 | 30 | 30 | 32 | 33 | 33 |
| 100 : | 0 : | 1 (#21235) | 0 | 3 | 5 | 5 | 5 | 5 | 5 |
| 100 : | 1 : | 1 (#21235) | 45 | 45 | 45 | 45 | 50 | 50 | 65 |
| 100 : | 0 : | 1 (#9226) | 12 | 8 | 7 | 7 | 8 | 7 | 5 |
| 100 : | 1 : | 1 (#9226) | 24 | 45 | 50 | 65 | 65 | 80 | 82 |

EXAMPLE 4

The procedure of Example 2 was followed, except that the oils used for testing were #4 heating oil, Southern Louisiana Crude, Prudhoe Bay Crude and La Rosa Crude. The results, shown in Table V, show that the synergistic effect of mixtures of small amounts of microorganism (in this instance, spray-dried ATCC 14,987) and chemical dispersant (in this instance, Mixture 2) holds for a variety of different oil samples. In each case, the mixture of microorganism plus chemical dispersant was far more effective than either agent alone.

EXAMPLE 5

The procedure of Example 4 was followed, except that the dispersant used was Mixture 3. The synergistic effect of mixtures of microorganism and chemical dispersant is once more apparent in the results (Table VI). Very little dispersion of La Rosa Crude was observed, but even in this instance, the mixture of microorganism and chemical dispersant was noticeably more effective than either agent alone.

TABLE V

| Ratio (By Wt.) Oil:Microorganism:Dispersant | | | % Dispersion After Various Times (Min.) | | | | | | |
|---|---|---|---|---|---|---|---|---|---|
| | (ATCC #14987) | Mixzture 2 | 5 | 15 | 30 | 45 | 60 | 90 | 120 |
| 100 (#4 Heating) | 1 | 0 | 15 | 28 | 28 | 23 | 17 | 20 | 18 |
| 100 (#4 Heating) | 0 | 1 | 10 | 10 | 15 | 13 | 15 | 15 | 10 |
| 100 (#4 Heating) | 1 | 1 | 40 | 42 | 60 | 75 | 75 | 65 | 60 |
| 100 (Southern Louisiana) | 1 | 0 | 26 | 25 | 30 | 35 | 35 | 34 | 30 |
| 100 (S. Louisiana) | 0 | 1 | 26 | 26 | 31 | 35 | 35 | 35 | 35 |
| 100 (S. Louisiana) | 1 | 1 | 54 | 60 | 83 | 77 | 75 | 70 | 65 |
| 100 (Prudhoe Bay) | 1 | 0 | 0 | 10 | 20 | 21 | 16 | 8 | 2 |
| 100 (Prudhoe Bay) | 0 | 1 | 35 | 40 | 25 | 18 | 16 | 8 | 10 |
| 100 (Prudhoe Bay) | 1 | 1 | 23 | 37 | 38 | 42 | 42 | 32 | 20 |
| 100 (La Rosa) | 1 | 0 | 0 | 0 | 5 | 8 | 10 | 7 | 8 |
| 100 (La Rosa) | 0 | 1 | 16 | 17 | 20 | 28 | 23 | 16 | 16 |
| 100 (La Rosa) | 1 | 1 | 22 | 36 | 47 | 72 | 60 | 45 | 40 |

TABLE VI

| Ratio (By Wt.) Oil:Microorganism:Dispersant | | | % Dispersion After Various Times (Min.) | | | | | | |
|---|---|---|---|---|---|---|---|---|---|
| | (ATCC #14987) | Mixture 3 | 5 | 15 | 30 | 45 | 60 | 90 | 120 |
| 100 (#4 Heating) | 1 | 0 | 15 | 30 | 28 | 23 | 17 | 20 | 10 |
| 100 (#4 Heating) | 0 | 1 | 10 | 10 | 15 | 12 | 10 | 10 | 10 |
| 100 (#4 Heating) | 1 | 1 | 40 | 42 | 60 | 75 | 75 | 62 | 60 |
| 100 (Southern Louisiana) | 1 | 0 | 30 | 34 | 34 | 35 | 30 | 25 | 25 |
| 100 (S. Louisiana) | 0 | 1 | 26 | 26 | 31 | 35 | 35 | 35 | 35 |
| 100 (S. Louisiana) | 1 | 1 | 54 | 60 | 84 | 77 | 75 | 70 | 64 |
| 100 (Prudhoe Bay) | 1 | 0 | 0 | 10 | 20 | 21 | 16 | 8 | 2 |
| 100 (Prudhoe Bay) | 0 | 1 | 20 | 19 | 17 | 13 | 10 | 16 | 14 |
| 100 (Prudhoie Bay) | 1 | 1 | 10 | 47 | 49 | 50 | 55 | 64 | 62 |
| 100 (La Rosa) | 1 | 0 | 0 | 0 | 5 | 8 | 6 | 5 | 6 |
| 100 (La Rosa) | 0 | 1 | 5 | 4 | 3 | 3 | 3 | 3 | 3 |
| 100 (La Rosa) | 1 | 1 | 13 | 16 | 16 | 16 | 16 | 18 | 20 |

EXAMPLE 6

Several other chemical dispersants were tested in another series of experiments. In these, the degree of dispersion of #4 heating oil was measured by determining particle size distributions, using a Coulter Counter, and calculating the percentage of oil present in the form of dispersed particles between 0.6 and 100 micron in diameter. The microbial preparation used was a lyophilized mixed culture, consisting of Arthrobacter sp. ATCC #21908, Micrococcus sp. ATCC #21909, and Achromobacter sp. ATCC #21910. The dispersion of #4 heating oil by the various materials at an oil:dispersant ratio of 100:10, after 1 hour, is shown in Table VII. Even though only half as much chemical dispersant was used in those flasks to which the microbial preparation was added (oil:dispersant:microorganism ratio was 100:5:25), the synergistic effect is again noted from the results in Table VII, wherein it can be seen that the combination of microorganisms plus dispersant was much more effective than the organisms or dispersant alone.

Table VII

| Ratio (By Wt.) | | % Dispersion After 1 Hour |
|---|---|---|
| Oil:Dispersant | Microorganism | |
| 100: 0: | 25 | 24 |
| 100:10 (COREXIT): | 0 | 5 |
| 100: 5 (COREXIT): | 25 | 57 |
| 100:10 (Ethomid): | 0 | 12 |
| 100: 5 (Ethomid): | 25 | 37 |
| 100:10 (Petrobac E): | 0 | 20 |
| 100: 5 (Petrobac E): | 25 | 59 |

Ethomid is a polyoxyethylene hydrogenated-tallow amide manufactured by Armour Ind. Chemical Company, Box 1805, Chicago, Illinois 60690. Petrobac E is a nonionic emulsifier manufactured by Enzymes Inc., 1100 Cornell Avenue, Cherry Hill, New Jersey 08034.

EXAMPLE 7

Additional tests were done using the microbial mixture of Example 6 and COREXIT as the chemical dispersant. As can be seen in Table VIII when the dispersant was used alone at an oil:dispersant ratio of 100:1, little if any, dispersion was observed. When small amounts of the microbial preparation were also added, a marked increase in the extent of dispersion was noted. Optimal dispersion was observed at an oil:dispersant-:microorganism ratio of 100:1:7; increasing the amount of microbial preparation further did not appear to be of much benefit.

TABLE VIII

| Ratio (By Wt.) | | | | % Dispersion After Various Times (Min.) | | |
|---|---|---|---|---|---|---|
| Oil: | Dispersant | : | Micro-organism | 60 | 120 | 150 |
| 100: | 1 | : | 0 | 8 | 11 | 14 |
| 100: | 1 | : | 1.75 | 25 | 63 | 68 |
| 100: | 1 | : | 3.5 | 23 | 68 | 68 |
| 100: | 1 | : | 7 | 43 | 83 | 93 |
| 100: | 1 | : | 14 | 43 | 83 | 91 |
| 100: | 1 | : | 28 | 51 | 83 | 88 |

EXAMPLE 8

The conditions of Example 7 were followed, except that in this instance, a freshly prepared 12 hour old microbial culture was substituted for the lyophilized material. The results, summarized in Table IX were similar. Once again, the dispersant alone at the low concentration used was ineffective; the addition small amounts of microorganisms markedly enhanced the dispersion.

TABLE IX

| Ratio (By Wt.) | | | | % Dispersion After Various Times (Min.) | |
|---|---|---|---|---|---|
| Oil: | Dispersant | : | Micro-organism | 60 | 120 |
| 100: | 1 | : | 0 | 6 | 10 |
| 100: | 1 | : | 1.75 | 56 | 70 |
| 100: | 1 | : | 3.5 | 40 | 58 |
| 100: | 1 | : | 7 | 78 | 82 |
| 100: | 1 | : | 14 | 65 | 75 |
| 100: | 1 | : | 28 | 53 | 68 |

What is claimed is:

1. A method for dispersing a layer of hydrocarbon oil in sea water, said hydrocarbon oil being selected from the group consisting of Kuwait crude, #4 heating oil, Prudhoe Bay crude and LaRosa crude which consists of contacting said oil layer with a chemical dispersant, said chemical dispersant consisting of 9 wt. % sorbitan monooleate, 15 wt. % sorbitan monooleate ethylene oxide adduct, 15 wt. % aqueous sodium dioctyl sulfosuccinate and 61 wt. % isoparaffinic solvent, said dispersant having an HLB of 10.6, in combination with the microorganism Micrococcus cerificans, said oil, dispersant and microorganism being contacted at a weight ratio of 100:1:1, said contacting being conducted at about 25° C.

2. A method for dispersing Kuwait crude in sea water which consists of contacting said Kuwait crude with a chemical dispersant consisting of 21 wt. % sorbitan monooleate, 7 wt. % sorbitan monooleate ethylene oxide adduct and 72 wt. % isoparaffinic hydrocarbon solvent, said dispersant having an HLB of 7.0, in combination with a microorganism selected from the group consisting of Corynebacterium and Candida utilis, said oil, dispersant and microorganism being contacted at a weight ratio of 100:1:1, said contacting being conducted at about 25° C.

3. A method for dispersing a layer of hydrocarbon oil in sea water, said hydrocarbon oil being selected from the group consisting of #4 heating oil, Prudhoe Bay crude and LaRosa crude, which method consists of contacting said oil layer with a chemical dispersant, said chemical dispersant consisting of 21 wt. % sorbitan monooleate, 7 wt. % sorbitan monooleate ethylene oxide adduct and 72 wt. % isoparaffinic hydrocarbon solvent, said chemical dispersant having an HLB of 7.0, in combination with the microorganism Micrococcus cerificans, said oil, dispersant and microorganism being contacted at a weight ratio of 100:1:1, said contacting being conducted at about 25° C.

* * * * *